(12) United States Patent
Marchetto (10) Patent No.: US 7,892,193 B2
(45) Date of Patent: Feb. 22, 2011

(54) OVERHEAD ACTIVITY HEAD-AND-NECK SUPPORT COLLAR

(76) Inventor: Donne Sebastian Marchetto, 5903 Farmview Ave., Baltimore, MD (US) 21206

( * ) Notice: Subject to any disclaimer, the term of this patent is extended or adjusted under 35 U.S.C. 154(b) by 283 days.

(21) Appl. No.: 12/102,241

(22) Filed: Apr. 14, 2008

(65) Prior Publication Data

US 2008/0251084 A1  Oct. 16, 2008

Related U.S. Application Data

(60) Provisional application No. 60/911,830, filed on Apr. 13, 2007.

(51) Int. Cl.
*A61F 5/00* (2006.01)
(52) U.S. Cl. .................................. 602/18; 128/DIG. 23
(58) Field of Classification Search ................. 128/845, 128/846, DIG. 19, DIG. 23; 602/18
See application file for complete search history.

(56) References Cited

U.S. PATENT DOCUMENTS

| | | | | |
|---|---|---|---|---|
| 4,858,249 A * | 8/1989 | Stewart | .......................... | 2/305 |
| 5,292,042 A * | 3/1994 | Yamaguchi et al. | ......... | 224/159 |
| 5,577,652 A * | 11/1996 | Cooper | ........................ | 224/578 |
| 5,628,772 A * | 5/1997 | Russell | ........................ | 607/109 |
| 5,738,640 A | 4/1998 | Carlson-Orsi | | |
| 6,130,616 A * | 10/2000 | Sizemore | ..................... | 340/574 |
| 6,217,366 B1 * | 4/2001 | Weisstock | .................... | 439/369 |
| 6,250,699 B1 * | 6/2001 | Robertson | .................... | 294/153 |
| 7,246,643 B2 * | 7/2007 | Andrews | ..................... | 150/105 |
| 7,448,682 B2 * | 11/2008 | Rutty | ....................... | 297/230.1 |

\* cited by examiner

*Primary Examiner*—Patricia M Bianco
*Assistant Examiner*—Camtu T Nguyen
(74) *Attorney, Agent, or Firm*—August Law, LLC; George Willinghan (57) ABSTRACT

A head-and-neck support collar is provided that supports the cervical region of the spine and the base of the skull when the head is in a tilted-back position. The collar is designed to reduce head-and-neck stress, strain and pain during physical activities that require the wearer to look upwards, especially for extended periods of time. The collar includes an elongated neck cushion that is positioned behind the neck of the user. A harness is attached to either end of the elongated neck cushion and is routed over the shoulders, under the arms and across the back. A two part quick release mechanism is provided between the harness and each end of the cushion to facilitate quick and complete release of the cushion from the harness. This quick release mechanism is preferably a hook and loop type fastener.

15 Claims, 6 Drawing Sheets

OVERHEAD ACTIVITY HEAD-AND-NECK SUPPORT COLLAR

CROSS-REFERENCE TO RELATED APPLICATIONS

The present application claims priority to provisional patent application No. 60/911,830 filed Apr. 13, 2007. The entire disclosure of that provisional application is incorporated herein by reference.

FIELD OF THE INVENTION

The present invention relates to orthopedic devices and in particular to cervical support devices.

BACKGROUND OF THE INVENTION

A wide variety of work and recreational activities require participants to look up for extended periods of time. For example, automobile mechanics working under a car that has been raised on a lift have to look up to work on the car. The person belaying for a rock climber must continuously look up at the climber during the entire time that the climber is ascending or descending. Since looking up requires tilting the head backwards, these activities can place strain on a participant's cervical and upper thoracic spine areas. Prolonged arching of the neck can lead to muscle strain and neck pain. Supports for the back of the head or cervical area should help to relieve the strain and fatigue and potentially avoid related cumulative stress injuries.

A wide variety of cervical support devices are known. Many of the devices are intended for medical or therapeutic purposes. These devices are typically constructed of rigid or soft materials such as plastic or foam and fabric. The device typically rests on the shoulders, supports the neck and holds the head-and-neck in a normal eyes (or face)-forward anatomical position. These devices are not well suited for relatively unrestricted physical activities and typically prevent the user from looking upwards. Other devices are intended to support the neck and head when the wearer is in a sitting or back-lying position. These devices are intended to provide support and proper alignment of the head-and-neck during rest or sleep. One such device is illustrated in U.S. Pat. No. 5,738,640. This device includes an upper cervical horizontal cushion, and an attached upper thoracic spine vertical cushion with straps to hold the device against the upper portion of the spine. It is intended to be used in a chair or bed with the wearer's head-and-neck resting against the chair or bed pillow. Again, this device is not intended to be used to provide neck support during physical activities. Because of the device's top-of-shoulder-straps attachment site onto the cervical (top or horizontal) component of this device's cushions, there is no effective forward pull and consequently that device would not successfully support the head-and-neck during upward-looking activities. In fact, the cervical horizontal cushion would effectively fall away from the back of the head-and-neck. Therefore, a head-and-neck support is desired that provides support for the back of the head-and-neck and is suitable for use during physical activities, especially during activities that require sustained extension of the cervical spine, i.e., looking-up activities.

SUMMARY OF THE INVENTION

The present invention is directed to a head-and-neck support collar that can be worn during physical activities and that provides support for the base of the skull and the posterior cervical region of the spine, i.e., the neck. Suitable activities for the use of this device include, but are not limited to, belaying in rock climbing, bird watching, astronomy, painting, dry-walling, seam-sealing overhead, continuously looking up from a wheelchair, car mechanics standing and working under cars overhead and electricians working overhead. The support collar includes an elongated neck cushion attached to a harness that includes a main strap. When the neck cushion is placed behind the neck, extending slightly upwards to the base of the skull, the main strap extends from either end of the neck cushion over the shoulders and behind the back. The strap only contacts the cushion at the ends, eliminating any other points of contact or back pieces that restrict movement. This end-of-cushion attachment of straps also provides for a forward pull on the cushion, thus allowing adequate support when the head-and-neck are in a tilted-back position.

In one embodiment, a webbed strap is sewn on either end of the cushion. Each short strap is threaded into a tensioning connector that allows for tightening and loosening of the cushion. Each tensioning connector is attached to one end of the main strap. From the tensioning connector, the webbing of the main strap continues over the shoulder, under the corresponding arm and across the back. The main strap proceeds from either tensioning connector using the same routing. Between the two tensioning connectors located at the ends of the main strap is a buckle. The buckle can be a snap connection and can include an additional tensioner.

In addition to the main strap, the harness can include a horizontal sternum or chest strap. The chest strap is constructed from a similar webbed belt material as the short straps and the main strap. The chest strap is connected to the main strap in two places between the ends of the main strap. In one embodiment, the chest strap includes a stair buckle. One end of the horizontal chest strap is laced through a male component of a snap buckle-tensioner, and the other end of the horizontal chest strap is laced through the female end of the snap buckle and is sewn back on itself, holding the female end of the snap buckle in place. The chest strap tensions the main strap and provides a point through which the harness and neck cushion can be put on or taken off.

The head-and-neck cushion supports the head-and-neck during cervical extension activities, i.e., head tilted-back activities. The cushion can be U-shaped to conform to the shape of the neck. In one embodiment, the cushion has a split-cylindrical shape with a generally flat side extending between the two ends and a generally rounded side opposite the flat side. In one embodiment, the rounded side is intended to be the surface making contact with the back of the neck and the base of the skull. The cushion is secured to the user by the harness. Having the attachment points on the ends of the cushion uniformly and conformingly draws the cushion around the neck when the tensioners or length adjusters in the harness are tightened.

In one embodiment, the harness holds the neck cushion in place and provides adjustability or tensioning. In another embodiment, the harness includes a quick-release mechanism that completely separates the harness from the neck cushion. In this tear-away safety harness embodiment, the collar can be torn-away in an emergency situation where a person would need to be quickly released from the setup. In one embodiment, the straps extending from the ends of the neck cushion are the first part of a two-part fastener, for example a hook-and-loop type fastener. In addition, the corresponding second parts of the two-part fastener are attached to either end of the main strap. Loops can also be provided near either end of the main strap to serve as handles to be used in the activating the quick release mechanism.

In accordance with one exemplary embodiment, the present invention is directed to a head-and-neck support collar that includes an elongated cushion having two opposing ends and a harness. In one embodiment, the cushion has a generally flat face running between the opposing ends and a generally rounded face opposite the flat face. The collar also includes two first parts of a two-part quick release mechanism. Each one of the two first parts is attached to and extends from one of the opposing ends of the elongated cushion. The harness includes a main strap having two ends and two second parts of the two-part quick release mechanism. Suitable materials for the main strap include polymer webbing. Each one of the two second parts is attached to one of the two main strap ends such that the elongated cushion and the main strap form a closed shape when each of the two first parts of the quick release mechanism is connected to one of the second parts of the quick release mechanism. This forms two separate quick release mechanisms, one each adjacent one of the opposing ends of the elongated cushion. The elongated cushion is completely disengaged from the harness when the first parts are released from the corresponding second parts of the quick release mechanism.

Preferably, the quick release mechanism is a hook and loop fastener. Suitable hook and loop type fasteners are available under the tradename Velcro® from Velcro Industries B.V. of Middlewich—Cheshire, UK. In this embodiment, the two first parts are each a loop portion of the hook and loop fastener, and the second parts are each a hook portion of the hook and loop fastener. In one embodiment, the harness includes a loop disposed at each end of the main strap. These loops provide a handle to engage the quick release mechanism. In one embodiment, the harness includes at least one length adjustment mechanism disposed between the two ends of the main strap. In one embodiment, the harness includes a buckle disposed between the two ends of the main strap. The buckle is separate from and independent of the two quick release mechanisms. The harness can also include a chest strap attached to the main strap at two distinct locations. The chest strap includes a buckle and a length adjustment mechanism and divides the closed shape of the cushion and strap into two closed shapes.

In one embodiment, the first parts of the two-part quick release mechanism each include a first length of a double-sided hook and loop fastener tape, and the second parts of the two-part quick release mechanism each include a second length of the double-sided hook and loop fastener tape. A portion of the second length of each second part is attached to a corresponding main strap end. In one embodiment, each second part is formed into a loop extending from the corresponding end of the main strap and having the hook portion of the hook and loop fastener tape on an exterior circumference. In one embodiment, each of the first lengths of the hook and loop fastener tape are equal to one half the circumference of the loops formed in the second parts. Each second length of the hook and loop fastener tape can include a portion between the end of the main strap and the loop having a length equal to one half the circumference of the loop.

The present invention is also directed to head-and-neck support collar having an elongated cushion having two opposing ends and a harness. The collar includes two first lengths of a double-sided hook and loop fastener tape. Each one of the two first lengths is attached to and extends from one of the opposing ends of the elongated cushion. The harness includes a main strap having two ends and two second lengths of the double-sided hook and loop fastener tape. Each one of the two second lengths is attached to one of the two main strap ends and includes a loop extending from a corresponding end of the main strap. The elongated cushion and main strap form a closed shape when each of the two first lengths is connected to one of the second lengths to form two separate quick release mechanisms. In addition, the elongated cushion is completely disengaged from the harness when the first lengths are released from the corresponding second lengths of the quick release mechanism. In one embodiment, each loop has a hook portion of the hook and loop fastener tape on an exterior circumference. In one embodiment, each of the first lengths is equal to one half the circumferences of the loops formed in the second length. In addition, each second length of the hook and loop fastener tape includes a portion between the end of the main strap and the loop having a length equal to one half the circumference of the loop.

DETAILED DESCRIPTION

Figure 1A:
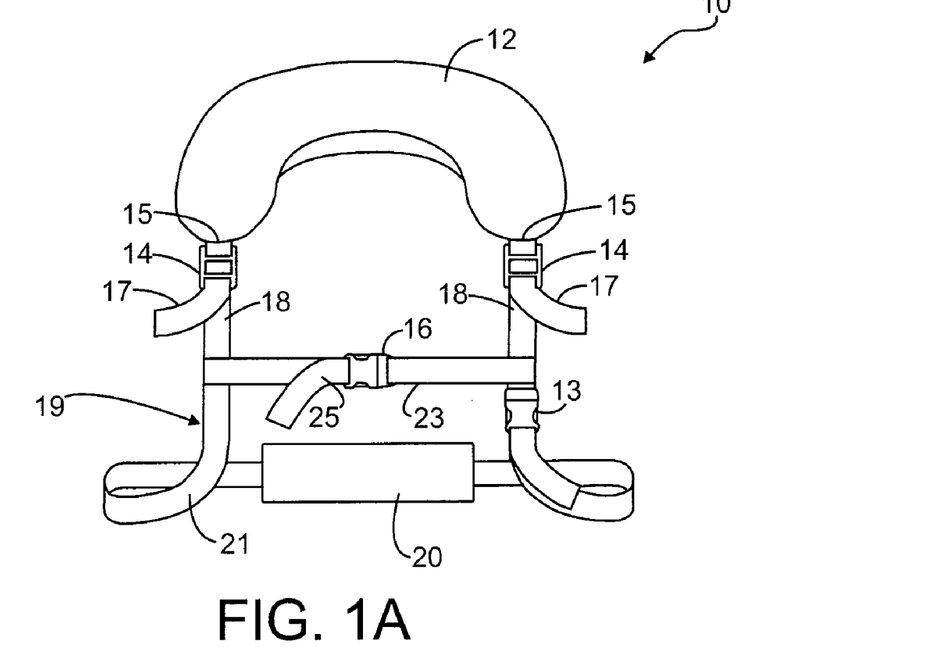
FIG. 1A is a front view of one embodiment of the head-and-neck support collar of the present invention.
Figure 4:
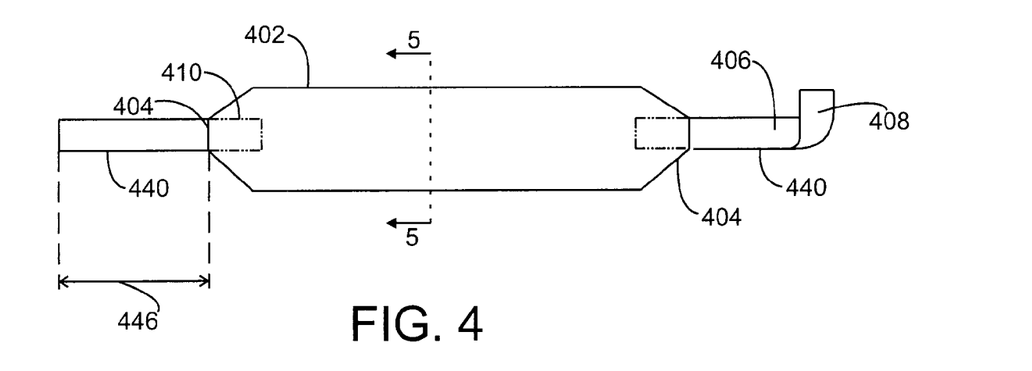
FIG. 4 is a top view of an embodiment of a neck cushion to be used in the head-and-neck support collar of the present invention.
Figure 5:
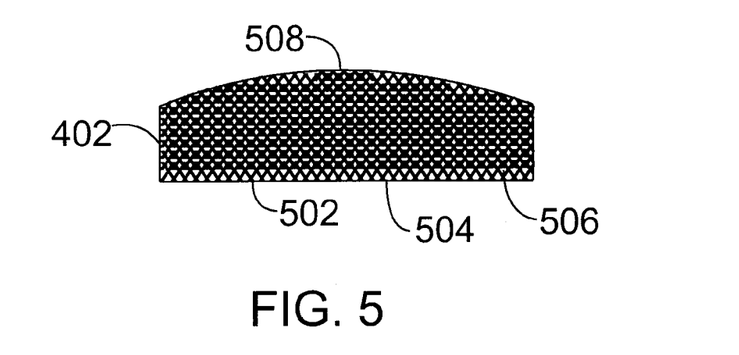
FIG. 5 is a view through line 5-5 of FIG. 4.

Referring initially to FIG. 1A, an exemplary embodiment of a head-and-neck support collar 10 in accordance with the present invention is illustrated. The head-and-neck support collar includes an elongated cushion 12 having two opposing ends 15. In one embodiment, the elongated cushion has a curved or U-shape that generally conforms to the contours of the neck of the user. Referring to FIGS. 4 and 5, in another embodiment, the elongated cushion 402 has a generally cylindrical or half-cylindrical shape having, for example, a flat surface 502 running between the two opposing ends 404 and a generally round or semi-circular surface 508 opposite the flat surface. The round surface is intended to make contact with the back of the neck and the base of the skull. In one embodiment, the elongated cushion is constructed of one or more cushioning materials 506 surrounded by a fabric cover. Suitable materials for the elongated cushion include foam rubber and polyester or other cushioning materials. Any suitable fabric can be used including natural and synthetic fabrics as well as fabric that provides for the wicking of moisture away from the skin. Alternatively, the cushion can be one piece molded foam rubber with a protective outer coating. Other suitable cushions include air bladders. In one embodiment, an additional removable cover (not shown) is placed over the cushion member.

Returning to FIG. 1A, in one embodiment, a short length of a webbing strap 17 is attached to each end of the cushion 12. Suitable webbing straps include synthetic or polymer webbings such as nylon webbing. This webbing, as well as all other strapping used herein can have a length of from about 0.5" up to about 1" and preferably about 0.75". The webbing strap is secured to the ends of the neck cushion using adhesives or stitching. In another embodiment, a first part of a two-part quick release mechanism is attached to each one of the ends of the elongated neck cushion. Any suitable two-part quick release mechanism can be used. Referring to FIG. 1C, in one embodiment, two first parts 40 of a two-part quick release mechanism are provided, and each one of the two first parts is attached to and extends from one of the opposing ends 15 of the elongated cushion. A preferred quick release mechanism is a two-part hook and loop type fastener. For example, synthetic webbing can be attached to the ends of the elongated cushion and the desired portion of the hook and loop fastener can be attached to the synthetic webbing, for example, using stitching. Alternatively, a tape containing the hook, the loop or both the hook and loop portion of the hook and loop fastener is attached to both of the opposing ends of the elongated cushion. In one embodiment, the first parts of the two-part quick release mechanism is the loop portion of the hook and loop fastener. Referring to FIG. 4, in one embodiment, the first parts 440 are double-sided hook and loop fastener tape having a loop portion 406 side and an opposing hook portion 408 side.

Returning to FIG. 1A, in one embodiment of the neck and head support collar 10, the collar includes a harness 19 that includes a main strap 21 having two ends 18. Suitable main straps include synthetic or polymer webbings such as nylon webbing. This webbing, as well as all other strapping used herein can have a width of from about 0.5" up to about 1" and preferably about 0.75". In this embodiment, tension adjusting clips 14 are provided at each of the two ends, and each tension adjusting clip accepts one of the two webbing straps 17 attached to the elongated cushion. A buckle 13 is included in the main strap between the two ends, and an optional expandable back strap 20 can also be provided between the two ends of the main strap. In one embodiment, the harness 19 includes a chest strap 23 attached to the main strap at two distinct locations. The chest strap 23 includes a buckle 16 and a length adjustment mechanism 25 and divides the closed shape of the cushion and strap into two closed shapes.

Figure 1B:
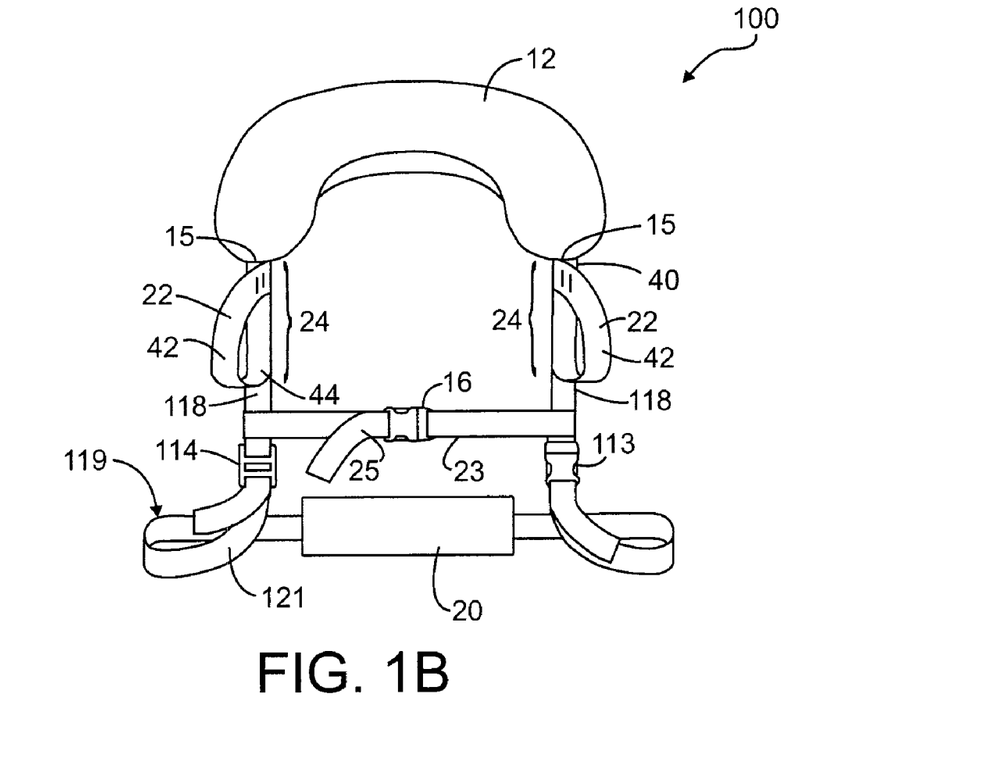
FIG. 1B is a front view of another embodiment of the head-and-neck support collar with a quick-release mechanism.
Figure 1C:
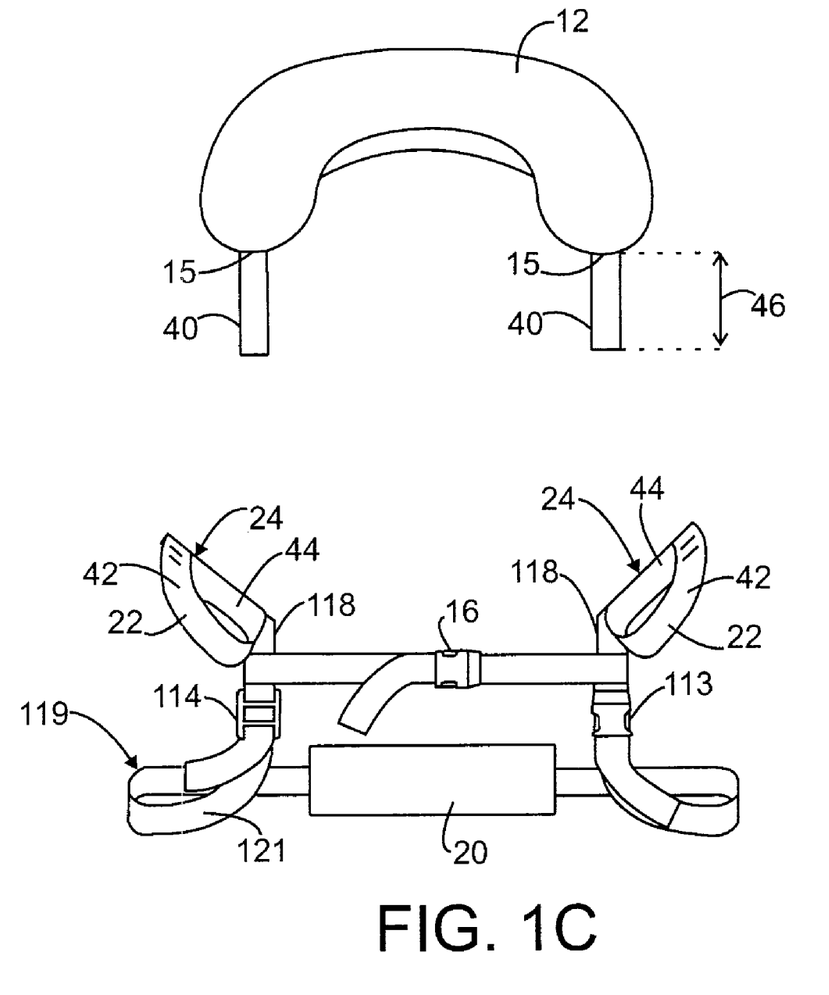
FIG. 1C is a front view of head-and-neck support collar with a quick-release mechanism with the neck cushion removed from the harness.

Referring to FIGS. 1B and 1C, in another embodiment the neck and head support collar 100 includes a harness 119 having a main strap 121 that includes two second parts 24 of the two-part quick release mechanism. Each one of the two second parts is attached to one of the two main strap ends 118. The elongated cushion 12 and main strap 121 form a closed shape (FIG. 1B) when each of the two first parts 40 of the quick release mechanism is connected to one of the second parts of the quick release mechanism 40, forming two separate quick release mechanisms. The elongated cushion 12 completely disengages from the harness 119 when the first parts 40 are released from the corresponding second parts 24 of the quick release mechanism (FIG. 1C). In one embodiment, the harness 119 includes a chest strap 23 attached to the main strap at two distinct locations. The chest strap 23 includes a buckle 16 and a length adjustment mechanism 25 and divides the closed shape of the cushion and strap into two closed shapes.

A preferred quick release mechanism is a two-part hook and loop type fastener, and in one embodiment, the second parts are the hook portion of the hook and loop type fastener. For example, the main strap 121 is constructed from synthetic webbing, and the desired portion of the hook and loop fastener can be attached to the synthetic webbing at the ends 118, for example, using stitching. Alternatively, a tape containing the hook, the loop or both the hook and loop portion of the hook and loop fastener is attached to both ends of the main strap. In one embodiment, each second part of the two-part quick release mechanism is the hook portion of the hook and loop fastener. In one embodiment, the second parts 24 are double-sided hook and loop fastener tape having a hook portion 42 side and an opposing loop portion side 44. A buckle 113 and a tension adjustment clip 114, i.e., a length adjustment mechanism, can be included in the main strap between the two ends, and an optional expandable back strap 20 can also be provided between the two ends of the main strap. The buckle is separate from and independent of the two quick release mechanisms.

In order to provide activation of the quick release mechanism, a handle or grip is provided for the user to grasp and to activate the quick release mechanism. This handle can take the form of a loop, for example, a loop of the main strap or a loop in the second part of the quick-release mechanism. As illustrated, the harness further includes a loop 22 disposed at each end of the main strap, each loop providing a handle to engage the quick release mechanism. In one embodiment, the first parts of the two-part quick release mechanism are a first length 46, 446 of a double-sided hook and loop fastener tape. This first length is the length of tape extending past the end of the neck cushion. Each first part may include additional lengths that are used for attaching the first parts to the ends of the cushion. The second parts of the two-part quick release mechanism are a second length of the double-sided hook and loop fastener tape. A portion of the second length of each second part is used for attachment to a corresponding main strap end. In one embodiment, each second part is formed into a loop 22 extending from the corresponding end of the main strap and having the hook portion of the hook and loop fastener tape on an exterior circumference 42. In one embodiment, each of the first lengths of the hook and loop fastener tape are equal to one half the circumference of the loops formed in the second parts. This length can be from about 4" to about 5".

Figure 6:
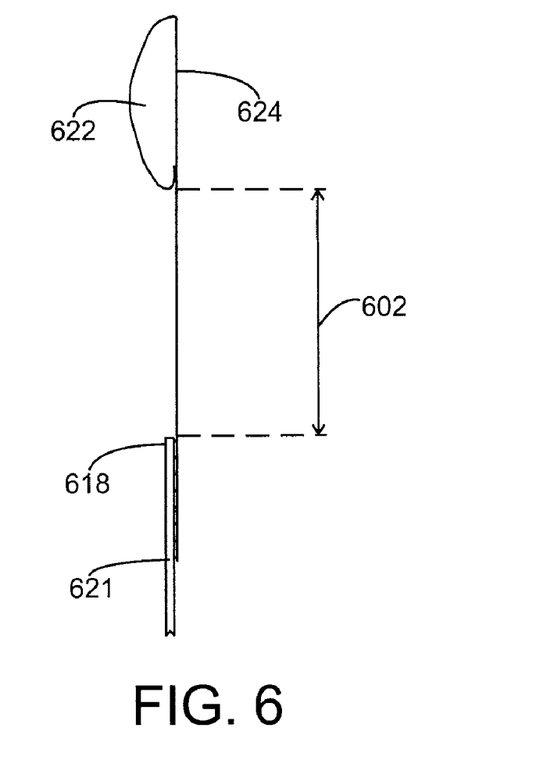
FIG. 6 is an illustration of an embodiment of a second part of a two part quick-release mechanism for use in the present invention.
Figure 7:
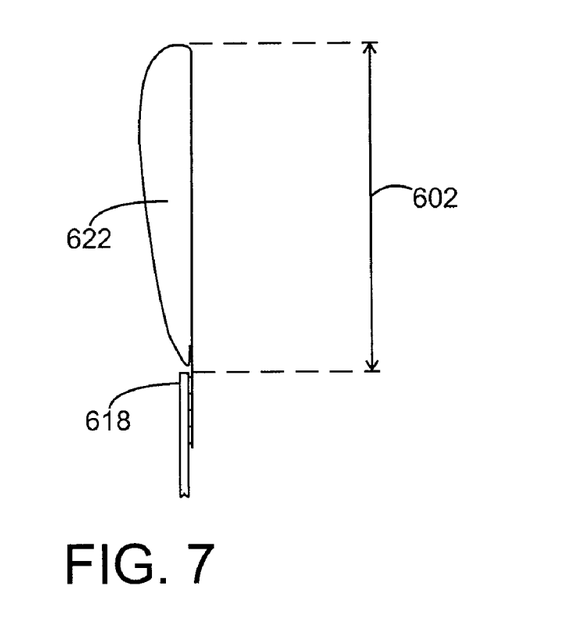
FIG. 7 is the illustration of FIG. 6, with the loop portion of the second part secured.

Referring to FIGS. 6 and 7, an embodiment of the second length of the second part 624 with the loop 622 is illustrated. In this embodiment, a second length of the hook and loop fastener tape includes a portion 602 of the tape between the end 618 of the main strap 621 and the loop 622 having a length equal to one half the circumference of the loop. This length is from about 4" to about 5". This length is also made of the double-side hook and loop fastener tape and allows the loop, i.e., the exterior circumference of the loop, to be secured against that portion of the tape as shown in FIG. 7.

Figures 2A, 2B, 2C:
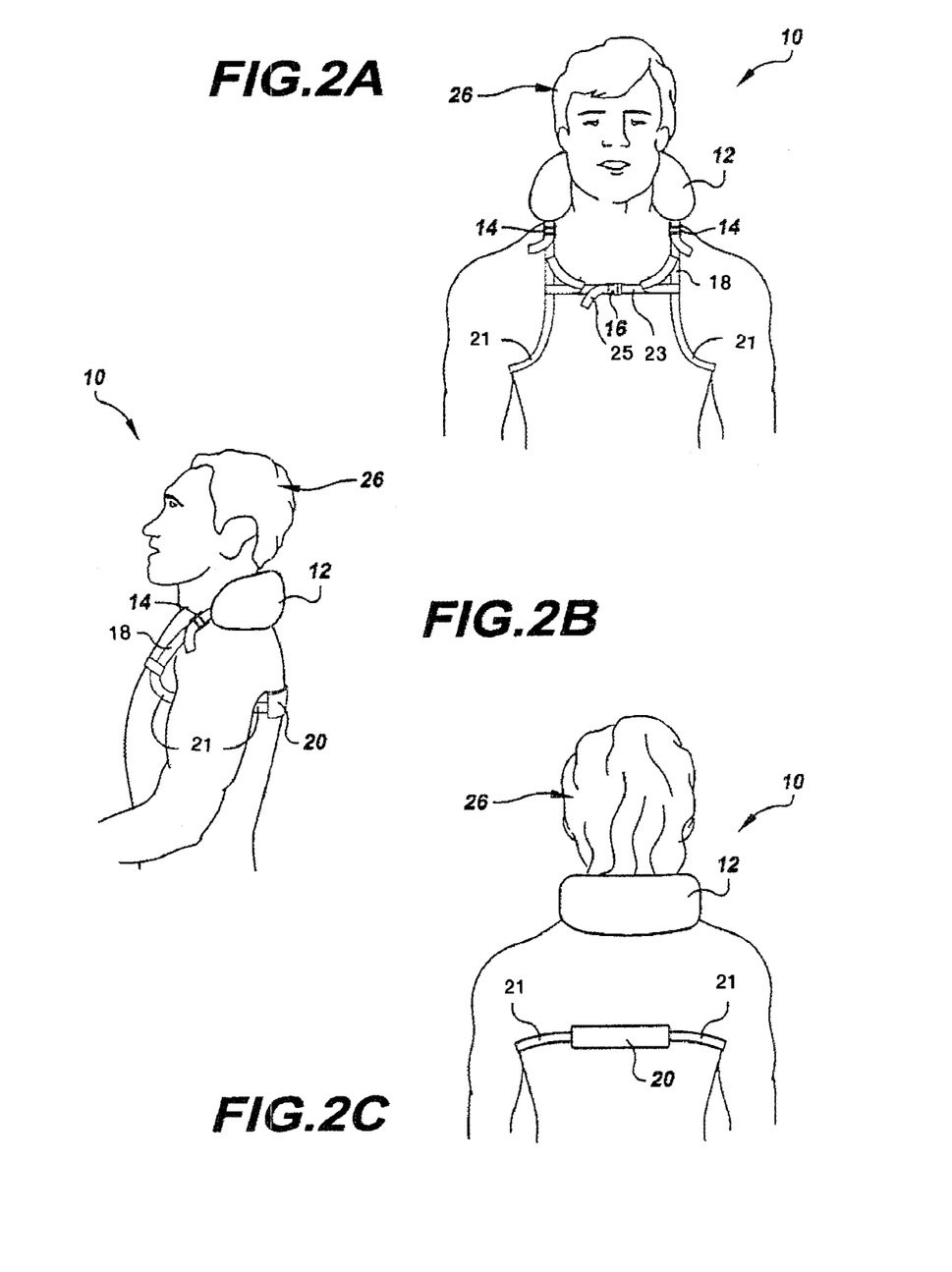
FIG. 2A is a front view of one embodiment of the head-and-neck support collar of the present invention attached to a user.
FIG. 2B is a side view of the embodiment of FIG. 2A attached to a user.
FIG. 2C is a back view of the embodiment of FIG. 2A attached to a user.
Figures 3A, 3B, 3C:
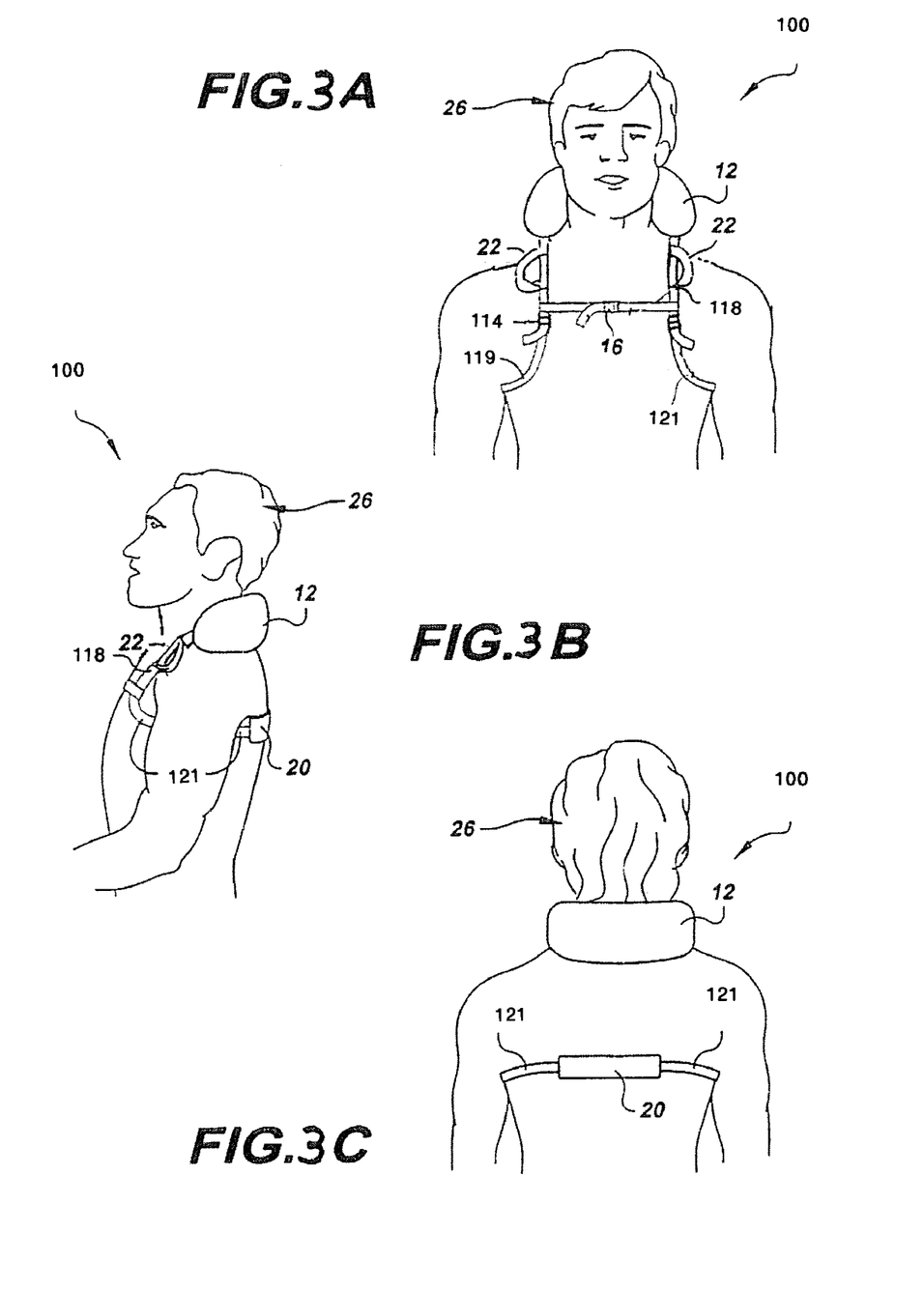
FIG. 3A is a front view of another embodiment of the head-and-neck support collar and quick-release mechanism of the present invention attached to a user.
FIG. 3B is a side view of the embodiment of FIG. 3A attached to a user.
FIG. 3C is a back view of the embodiment of FIG. 3A attached to a user.

FIGS. 2A, 2B and 2C illustrate a first embodiment of the head-and-neck support collar of the present invention attached to a user 26. FIGS. 3A, 3B and 3C illustrate a second embodiment of the head-and-neck support collar with the quick release mechanism of the present invention attached to a user 26. The neck cushion is placed behind the neck of the user, and the main strap is routed over the shoulders, under the arms and behind the back of the user. The length can be adjusted as desired, and this adjustment, since it is pulling forward on the ends of the neck cushion, conforms the cushion to the back of the user's neck, extending partially to each side of the user's cervical region, i.e., neck. There is no connection between the main strap and the neck cushion behind the user, and no pads or straps run vertically up the spine between the shoulder blades. This provides a greater degree of unobstructed movement to both the head and arms. The quick release mechanism is located in front of the user on the upper chest. This placement makes it easy for the user to access and to activate the quick release mechanism.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A head and neck support collar comprising:
   an elongated cushion having two opposing ends;
   two first parts of a two-part quick release mechanism, each one of the two first parts attached to and extending from one of the opposing ends of the elongated cushion;
   a harness comprising a main strap comprising two ends and two second parts of the two-part quick release mechanism, each one of the two second parts attached to one of the two main strap ends, the elongated cushion and main strap forming a closed shape when each of the two first parts of the quick release mechanism is connected to one of the second parts of the quick release mechanism to form two separate quick release mechanisms and the elongated cushion completely disengaged from the harness when the first parts are released from the corresponding second parts of the quick release mechanism;
   wherein the harness further comprises a chest strap attached to the main strap at two distinct locations, the chest strap comprising a buckle and a length adjustment mechanism and dividing the closed shape of the cushion and strap into two closed shapes, and a loop disposed at each end of the main strap, each loop providing a handle to engage the quick release mechanism.

2. The head and neck support collar of claim 1, wherein the quick release mechanism comprises a hook and loop fastener.

3. The head and neck support collar of claim 2, wherein the two first parts comprise a loop portion of the hook and loop fastener and the two second parts comprise a hook portion of the hook and loop fastener.

4. The head and neck support collar of claim 1, wherein the cushion comprises a generally flat face running between the opposing ends and a generally rounded face opposite the flat face.

5. The head and neck support collar of claim 1, wherein the harness further comprises at least one length adjustment mechanism disposed between the two ends of the main strap.

6. The head and neck support collar of claim 1, wherein the harness further comprises a buckle disposed between the two ends of the main strap, the buckle separate from and independent of the two quick release mechanisms.

7. The head and neck support collar of claim 1, wherein the first parts of the two-part quick release mechanism each comprise a first length of a double-sided hook and loop fastener tape and the second parts of the two-part quick release mechanism each comprise a second length of the double-sided hook and loop fastener tape, a portion of the second length of each second part attached to a corresponding main strap end.

8. The head and neck support collar of claim 7, wherein each second part is formed into a loop extending from the corresponding end of the main strap and having the hook portion of the hook and loop fastener tape on an exterior circumference.

9. The head and neck support collar of claim 8, wherein each of the first lengths of the hook and loop fastener tape are equal to one half the circumference of the loops formed in the second parts.

10. The head and neck support collar of claim 8, wherein each second length of the hook and loop fastener tape includes a portion between the end of the main strap and the loop having a length equal to one half the circumference of the loop.

11. The head and neck support collar of claim 7, wherein the main strap comprises a polymer webbing.

12. A head and neck support collar comprising:
   an elongated cushion having two opposing ends;
   two first lengths of a double-sided hook and loop fastener tape, each one of the two first lengths attached to and extending from one of the opposing ends of the elongated cushion; and
   a harness comprising a main strap comprising two ends and two second lengths of the double-sided hook and loop fastener tape, each one of the two second lengths attached to one of the two main strap ends and comprising a loop extending from a corresponding end of the main strap, the elongated cushion and main strap forming a closed shape when each of the two first lengths is connected to one of the second lengths to form two separate quick release mechanisms and the elongated cushion completely disengaged from the harness when the first lengths are released from the corresponding second lengths of the quick release mechanism;
   wherein each loop has a hook portion of the hook and loop fastener tape on an exterior circumference.

13. The head and neck support collar of claim 12, wherein each of the first lengths are equal to one half the circumference of the loops formed in the second length.

14. The head and neck support collar of claim 12, wherein each second length of the hook and loop fastener tape includes a portion between the end of the main strap and the loop having a length equal to one half the circumference of the loop.

15. A head and neck support collar comprising:
   an elongated cushion having two opposing ends;
   two first lengths of a double-sided hook and loop fastener tape, each one of the two first lengths attached to and extending from one of the opposing ends of the elongated cushion; and
   a harness comprising a main strap comprising two ends and two second lengths of the double-sided hook and loop fastener tape, each one of the two second lengths attached to one of the two main strap ends and comprising a loop extending from a corresponding end of the main strap, the elongated cushion and main strap forming a closed shape when each of the two first lengths is connected to one of the second lengths to form two separate quick release mechanisms and the elongated cushion completely disengaged from the harness when the first lengths are released from the corresponding second lengths of the quick release mechanism;
   wherein each of the first lengths is equal to one half the circumference of the loops formed in the second length.

\* \* \* \* \*